United States Patent
Ohyu et al.

(10) Patent No.: US 8,350,566 B2
(45) Date of Patent: Jan. 8, 2013

(54) MAGNETIC PARTICLE IMAGING APPARATUS, METHOD OF DISPOSING DETECTION COIL FOR MAGNETIC PARTICLE IMAGING APPARATUS, AND MAGNETIC FLUX DETECTING APPARATUS

(75) Inventors: Shigeharu Ohyu, Yaita (JP); Motoji Haragashira, Utsunomiya (JP); Yasuo Sakurai, Otawara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 301 days.

(21) Appl. No.: 12/138,132

(22) Filed: Jun. 12, 2008

(65) Prior Publication Data

US 2008/0309330 A1 Dec. 18, 2008

(30) Foreign Application Priority Data

Jun. 15, 2007 (JP) ................ 2007-158546

(51) Int. Cl.
*G01V 3/00* (2006.01)

(52) U.S. Cl. ........ 324/300; 324/309; 324/318; 324/313; 324/314

(58) Field of Classification Search ........ 324/228, 324/232, 300–322; 345/107; 382/128–131; 600/407–435
See application file for complete search history.

(56) References Cited

U.S. PATENT DOCUMENTS

| | | | | |
|---|---|---|---|---|
| 5,411,398 A | * | 5/1995 | Nakanishi et al. | 434/409 |
| 7,081,753 B2 | * | 7/2006 | Mullen et al. | 324/318 |
| 7,482,807 B2 | * | 1/2009 | Gleich et al. | 324/309 |
| 8,044,660 B2 | * | 10/2011 | Gleich et al. | 324/228 |
| 2006/0008924 A1 | * | 1/2006 | Anker et al. | 436/526 |
| 2006/0009826 A1 | | 1/2006 | Gleich | |
| 2006/0248945 A1 | * | 11/2006 | Gleich | 73/53.01 |
| 2008/0204009 A1 | * | 8/2008 | Gleich et al. | 324/228 |
| 2008/0309330 A1 | * | 12/2008 | Ohyu et al. | 324/232 |
| 2010/0033174 A1 | * | 2/2010 | Gleich et al. | 324/228 |
| 2010/0045280 A1 | * | 2/2010 | Gleich et al. | 324/228 |
| 2010/0123456 A1 | * | 5/2010 | Boeve et al. | 324/228 |
| 2011/0241663 A1 | * | 10/2011 | Gleich | 324/244 |

FOREIGN PATENT DOCUMENTS

| | | |
|---|---|---|
| CN | 1774200 A | 5/2006 |
| JP | 63-286143 A | 11/1988 |
| JP | 2003-199767 | 7/2003 |

(Continued)

OTHER PUBLICATIONS

B. Gleich et al., "Magnetic Particle Imaging (MPI)", Investigations and Research, MEDICAMUNDI 50/1, May 2006, pp. 66-71.
Bernhard Gleich et al., "Tomographic imaging using the nonlinear response of magnetic particles", Nature, Letters, vol. 435, doi:10.1038/nature03808, Jun. 30, 2005, pp. 1214-1217.

(Continued)

*Primary Examiner* — Melissa Koval
*Assistant Examiner* — Tiffany Fetzner
(74) *Attorney, Agent, or Firm* — Oblon, Spivak, McClelland, Maier & Neustadt, L.L.P.

(57) ABSTRACT

In a magnetic particle imaging apparatus that forms an image of a distribution of magnetic particles based on changes in a magnetic flux generated by magnetization of the magnetic particles, modulation coils that magnetize magnetic particles present in a field free area by applying a modulation magnetic field to the field free area, and detection coils are disposed such as to suppress an influence caused by a magnetic flux of the modulation magnetic field applied by the modulation coils and included in a detected magnetic flux.

23 Claims, 14 Drawing Sheets

FOREIGN PATENT DOCUMENTS

| | | |
|---|---|---|
| JP | 2006-523491 | 10/2006 |
| JP | 2006-523494 | 10/2006 |
| JP | 2006-523495 | 10/2006 |
| JP | 2006-523496 | 10/2006 |
| JP | 2006-524081 | 10/2006 |
| JP | 2006-525506 | 11/2006 |
| WO | WO 2004/091390 A2 | 10/2004 |
| WO | WO 2004/091392 A1 | 10/2004 |
| WO | WO 2004/091396 A2 | 10/2004 |
| WO | WO 2004/091397 A2 | 10/2004 |
| WO | WO 2004/091398 A2 | 10/2004 |
| WO | WO 2004/091721 A1 | 10/2004 |
| WO | WO/2007/000350 | 1/2007 |

OTHER PUBLICATIONS

J. Weizenecker et al, "A simulation study on the resolution and sensitivity of magnetic particle imaging", IOP Publishing, Physics in Medicine and Biology, vol. 52, doi:10.1088/0031-9155/52/21/001, 2007, pp. 6363-6374.

B. Gleich et al., "Experimental results on fast 2D-encoded magnetic particle imaging", IOP Publishing, Physics in Medicine and Biology, vol. 53, doi:10.1088/0031-9155/53/6/N01, 2008, pp. N81-N84.

Japanese Office Action issued Jun. 5, 2012 in Patent Application No. 2007-158546 with English Translation.

* cited by examiner

MAGNETIC FIELD GENERATED BY PERMANENT MAGNETS IN VERTICAL CENTER

SCAN COILS APPLY MAGNETIC FIELD FLOWING RIGHT

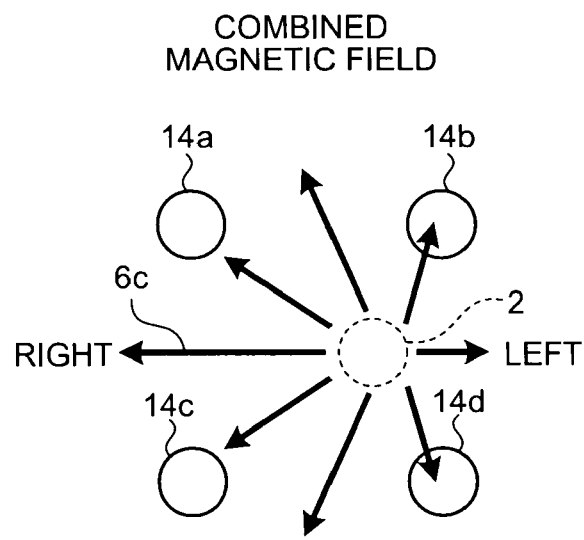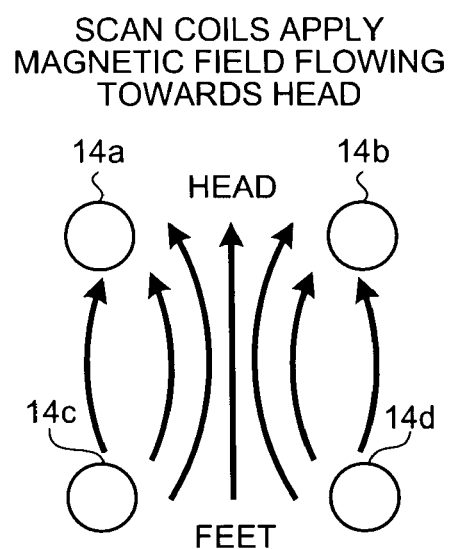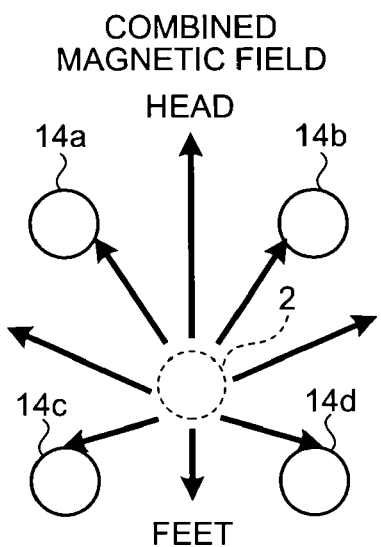

INTENSITY H OF MAGNETIC FIELD AT
FIELD FREE AREA

MAGNETIC FIELD B AT FIELD FREE AREA

MAGNETIZATION M AT FIELD FREE AREA

MAGNETIC PARTICLE IMAGING APPARATUS, METHOD OF DISPOSING DETECTION COIL FOR MAGNETIC PARTICLE IMAGING APPARATUS, AND MAGNETIC FLUX DETECTING APPARATUS

CROSS-REFERENCE TO RELATED APPLICATIONS

This application is based upon and claims the benefit of priority from the prior Japanese Patent Application No. 2007-158546, filed on Jun. 15, 2007; the entire contents of which are incorporated herein by reference.

BACKGROUND OF THE INVENTION

1. Field of the Invention

The present invention relates to a magnetic particle imaging apparatus that forms an image of a distribution of magnetic particles based on change in magnetic flux caused by magnetization of the magnetic particles, a method of disposing a detection coil for the magnetic particle imaging apparatus, and a magnetic flux detecting apparatus. In particular, the present invention relates to a technology for enhancing detection sensitivity of the detection coil.

2. Description of the Related Art

In recent years, a method has been proposed for injecting magnetic particles, such as super paramagnetic iron oxide, that serve as a contrast medium into a subject and forming an image of a distribution of the contrast medium (refer to, for example, JP-A 2003-199767 (KOKAI) or B. Gleich, J. Borgert, J. Weizenecker, "Magnetic Particle Imaging (MPI)", Philips Medic Mundi Vol. 50 No. 1, 2006/5 [online], May 23, 2007, retrieved from the Internet: URL: http://www.medical.philips.com/main/news/assets/docs/medi camundi/mm_vol50_no1/12_Gleich.pdf). This method is called magnetic particle imaging. FIG. 16 is a diagram for explaining a principle of magnetic particle imaging. In magnetic particle imaging, for example, a static magnetic field 1 flowing in vertically opposite directions is generated using a permanent magnet in an area in which magnetic particles are distributed.

At this time, a magnetic field from above and a magnetic field from below are mutually cancelled at an approximate center of the static magnetic field 1, thereby generating an area 2 where a localized magnetic field becomes zero. The area 2 is referred to as a "field free area". Then, a modulation coil 4 for generating a modulation magnetic field and a detection coil 5 for detecting a change in an interlinking magnetic flux are disposed within the static magnetic field 1.

Here, it is assumed that a modulation magnetic field 3 is generated in the area in which the magnetic particles are distributed by applying an electrical current to the modulation coil 4. At this time, magnetic saturation occurs in areas other than the field free area 2 because of the static magnetic field 1. Therefore, the magnetic flux within the areas other than the field free area 2 does not change even when the modulation magnetic field 3 is applied. On the other hand, magnetic saturation does not occur in the field free area 2 because the magnetic field is near to zero. When the modulation magnetic field 3 is applied, the magnetic particles present in the field free area 2 become magnetized. A magnetic flux is generated from the field free area 2 with the magnetization of the magnetic particles.

The magnetic flux generated from the field free area 2 causes a change in the magnetic flux interlinked with the detection coil 2. The change in the magnetic flux appears as a change in voltage induced in the detection coil 5. An amount of change in the voltage depends on an amount of magnetic particles present in the field free area 2. In other words, the voltage induced in the detection coil 5 changes based on the amount of magnetic particles present in the field free area 2.

When the above-described principle is used, an image of the distribution of the magnetic particles within the subject can be formed by measuring a change in the voltage induced in the detection coil being measured while the field free area is gradually moved within the subject into which the magnetic particles have been injected. In recent years, a deliberation has begun on clinical application of the above-described magnetic particle imaging.

In the above-described magnetic particle imaging, the change in the voltage induced by the magnetization of the magnetic particles is required to be measured using the detection coil. However, voltage caused by the modulation magnetic field applied by the modulation coil is also induced in the detection coil. The detection coil detects voltage as a modulation signal (such as high-frequency signal). However, when the voltage caused by the modulation magnetic field is also induced, a signal indicating the change in the voltage caused by the magnetization of the magnetic particles and a signal indicating change in the voltage caused by the modulation magnetic field are detected in an overlapping state. Therefore, when an image of the distribution of the magnetic particles is formed, it is required to extract only the signal of the voltage induced by the magnetization of the magnetic particles from the signals detected by the detection coil.

However, the voltage induced by the modulation magnetic field is significantly larger than the voltage induced by the magnetic particles. Therefore, separation of the respective signals of the voltages becomes difficult. This problem becomes more significant in clinical application.

For example, when a magnetic particle imaging apparatus scaled for humans is configured based on a description written in "Magnetic Particle Imaging (MPI)" by B. Gleich, J. Borgert, and J. Weizenecker, and it is assumed that a magnitude of the modulation magnetic field applied by the modulation coil is $10\,mT/\mu_0$, that is a strength facilitating magnetic saturation of the magnetic particles, the voltage induced in the detection coil by the modulation magnetic field is about 150 volts. On the other hand, for example, when an early stage cancer cell of $10\,mm^3$ indicating diamagnetism having a magnetic susceptibility of $-7.1 \times 10^{-6}$ is the subject, the voltage induced in the detection coil is about 50 nanovolts.

A known document describes a separation method using frequency as a method for separating the signals. Specifically, the method takes advantage of the signal of the voltage induced by the magnetization of the magnetic particles including distortion, whereas the signal of the voltage induced by the modulation magnetic field is a sine wave. A harmonic component is extracted from the signals detected by the detection coil. As a result, only the signal of the voltage induced by the magnetization of the magnetic particles is extracted.

However, when taking into consideration of clinical application, because the voltage induced by the modulation magnetic field is significantly larger than the voltage induced by the magnetization of the magnetic particles, as described above, it id difficult to obtain sufficient detection sensitivity even using this method. Therefore, to apply the magnetic particle imaging to a clinical application, the detection sensitivity of the detection coil is required to be significantly enhanced compared to a conventional detection coil.

SUMMARY OF THE INVENTION

According to one aspect of the present invention, a magnetic particle imaging apparatus includes a magnet unit that generates a magnetic field such as to form a non-magnetic field area within a detection space; a modulation coil that magnetizes magnetic particles by applying a modulation magnetic field; a detection coil that detects a change in a magnetic flux interlinked with the detection coil and is disposed such as to suppress an influence caused by a magnetic flux of the modulation magnetic field applied by the modulation coil and included in the detected magnetic flux; and an image processing unit that forms an image of a distribution of the magnetic particles based on the change in the magnetic flux detected by the detection coil.

According to another aspect of the present invention, a method of disposing detection coil for a magnetic particle imaging apparatus, the method includes disposing a modulation coil that magnetizes magnetic particles by applying a modulation magnetic field and a detection coil that detects a change in a magnetic flux interlinked with the detection coil, such that an influence caused by a magnetic flux of the modulation magnetic field applied by the modulation coil and included in the detected magnetic flux is suppressed.

According to still another aspect of the present invention, a magnetic flux detecting apparatus includes a modulation coil that magnetizes magnetic particles by applying a modulation magnetic field; and a detection coil that detects a change in a magnetic flux interlinked with the detection coil, and that is disposed such that an influence caused by a magnetic flux of the modulation magnetic field applied by the modulation coil and included in the detected magnetic flux is suppressed.

BRIEF DESCRIPTION OF THE DRAWINGS

FIGS. 3A to 3F are diagrams for explaining zero magnetic-field scan coils;

DETAILED DESCRIPTION OF THE INVENTION

Exemplary embodiments of a magnetic particle imaging apparatus, a method of disposing a detection coil for the magnetic particle imaging apparatus, and a magnetic flux detecting apparatus according to the present invention are below described with reference to the attached drawings.

Figure 1:
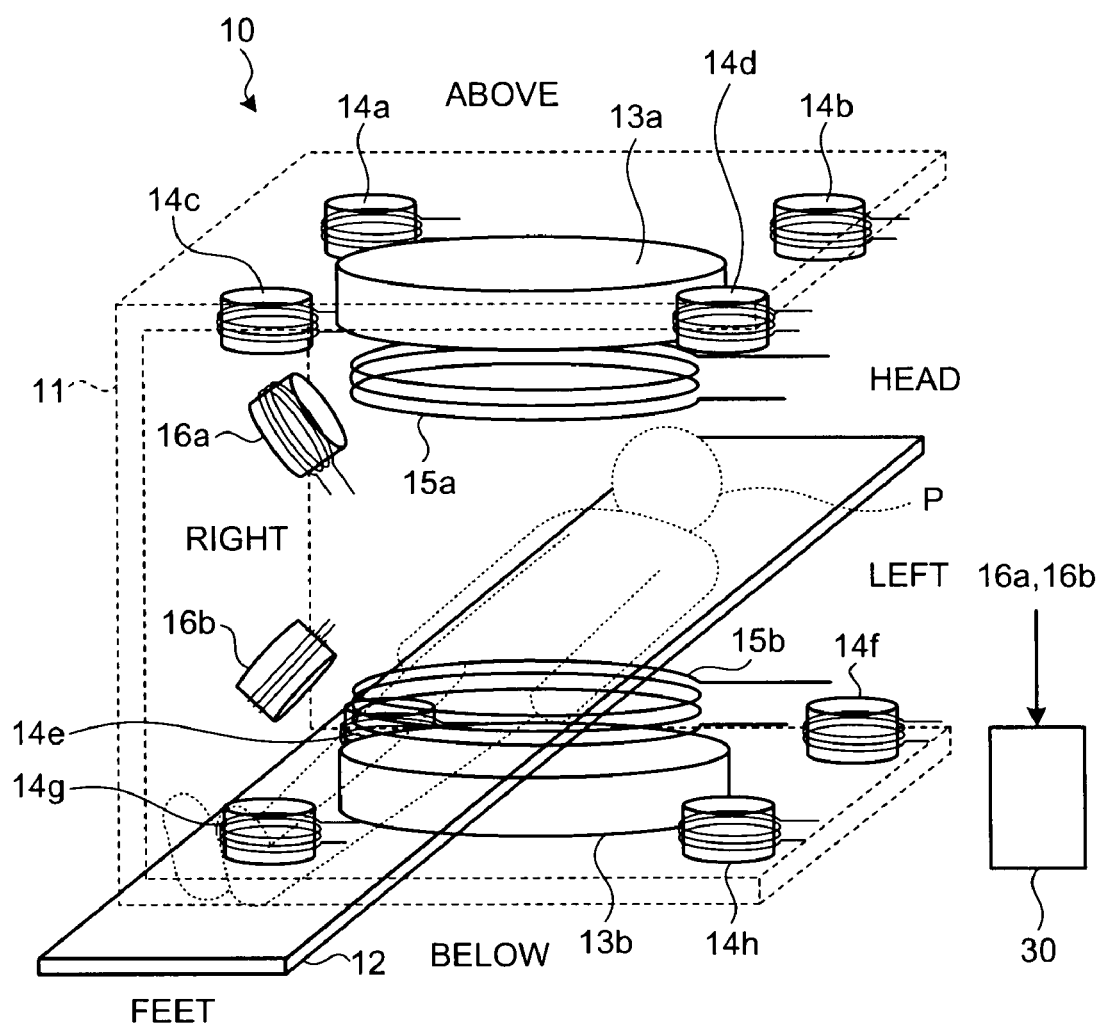
FIG. 1 is a perspective view of a configuration of a magnetic particle imaging apparatus according to a first embodiment.

FIG. 1 is a perspective view of a configuration of a magnetic particle imaging apparatus according to a first embodiment. As shown in FIG. 1, a magnetic particle imaging apparatus 10 includes a frame 11, a top plate 12, permanent magnets 13a and 13b, zero magnetic-field scan coils 14a to 14h, modulation coils 15a and 15b, detection coils 16a and 16b, and an image processing unit 30.

The frame 11 is a u-shaped component and supports the permanent magnets 13a and 13b, the zero magnetic-field scan coils 14a to 14h, the modulation coils 15a and 15b, and the detection coils 16a and 16b.

The top plate 12 is a plate-shaped component provided in an approximate center of an area surrounded by the frame 11. A subject P (such as a patient) to be imaged is placed on the top plate 12. The top plate 12 is moved by an apparatus (not shown). Here, directions above and below, right and left, and head and feet are defined based on the subject P placed on the top plate 12 on his back.

Figure 2A:
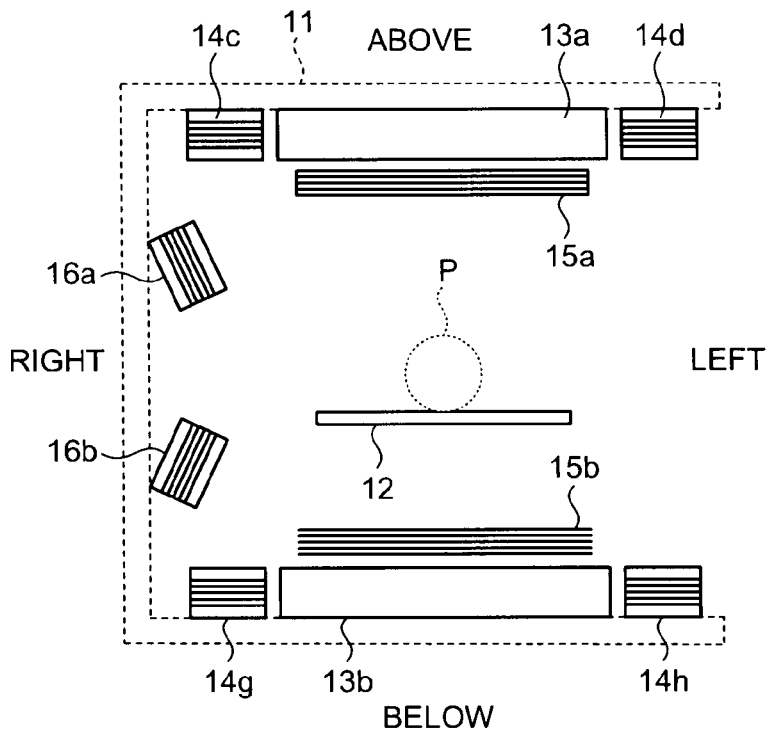
FIGS. 2A and 2B are diagrams for explaining permanent magnets.
Figure 2B:
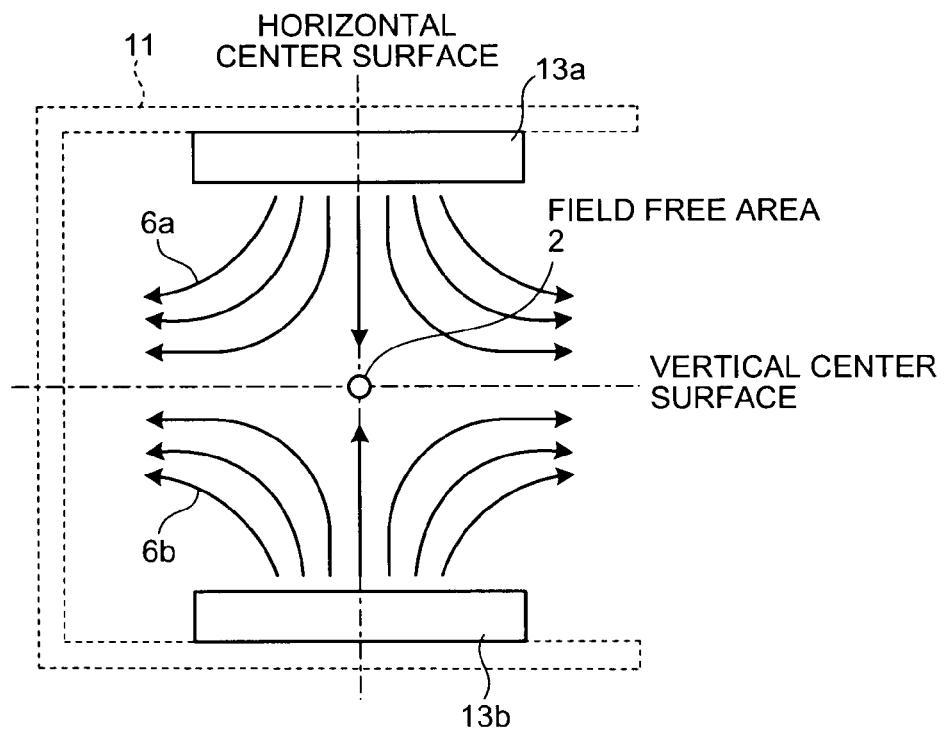

The permanent magnets 13a and 13b are magnets used to generate a field free area within the frame 11. FIGS. 2A and 2B are diagrams for explaining the permanent magnets 13a and 13b. As shown in FIG. 2A, the permanent magnets 13a and 13b are respectively disposed on an upper surface and a lower surface of an inner wall of the frame 11. The permanent magnets 13a and 13b are disposed facing each other.

The permanent magnets 13a and 13b are disposed such that respectively generated magnetic fields flow in opposite directions. As a result of the permanent magnets 13a and 13b being disposed in this way, as shown in FIG. 2B, a magnetic field 6a generated by the permanent magnet 13a and a magnetic field 6b generated by the permanent magnet 13b are mutually cancelled at the middle point of the permanent magnet 13a and 13b, thereby generating a field free area 2.

Here, as shown in the diagrams, a surface passing through a center of the field free area 2 and dividing the area surrounded by the frame 11 into left and right is referred to as a "horizontal center surface". A surface passing through the center of the field free area 2 and dividing the area surrounded by the frame 11 into top and bottom is referred to as a "vertical center surface".

Figure 3A:
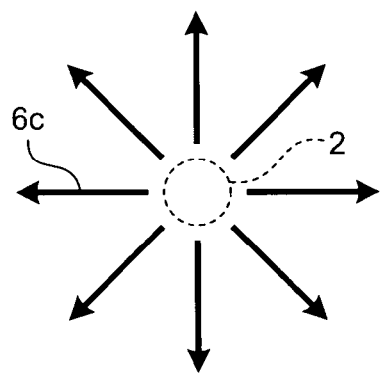

The zero magnetic-field scan coils 14a to 14h are electromagnets used to control a position of the field free area 2. FIGS. 3A to 3F are diagrams for explaining the zero magnetic-field scan coils 14a to 14h. FIG. 3A shows a state of a magnetic field on the vertical center surface shown in FIG. 2B. As shown in FIG. 3A, on the vertical center surface, a magnetic field 6c is generated that is a combination of the magnetic field 6a and the magnetic field 6b shown in FIG. 2B. The field free area 2 is generated in a center portion of the magnetic field 6c.

Figure 3B:
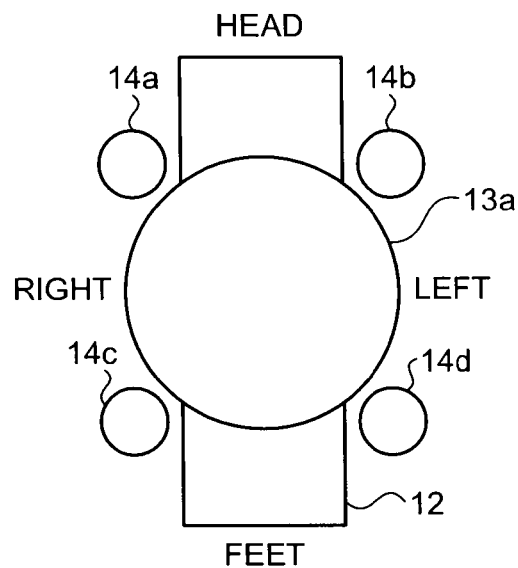

FIG. 3B shows the top plate 12, the permanent magnet 13a disposed on an upper surface of the inner wall of the frame 11, and the zero magnetic-field scan coils 14a to 14d. As shown in FIG. 3B, the zero magnetic-field scan coils 14a to 14d are disposed around the permanent magnet 13a.

Specifically, a zero magnetic-field scan coil 14a is disposed on a right side of a head end from the perspective of the subject P. A zero magnetic-field scan coil 14b is disposed on a left side of the head end. A zero magnetic-field scan coil 14c is disposed on the right side of a feet end. A zero magnetic-field scan coil 14d is disposed on the left side of the feet end.

Figure 3C:
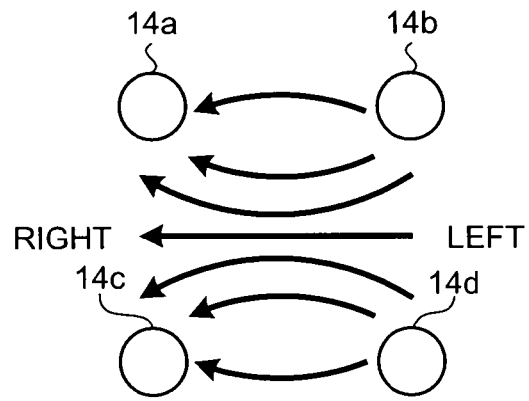

For example, it is assumed that electric current flowing through each zero magnetic-field scan coil is adjusted such that a magnetic field flowing from the zero magnetic-field scan coil 14b towards the zero magnetic-field scan coil 14a and a magnetic field flowing from the zero magnetic-field scan coil 14d towards the zero magnetic-field scan coil 14c are generated. In this case, as shown in FIG. 3C, a magnetic field flowing from the left side to the right side is generated. When the generated magnetic field and the magnetic field 6c shown in FIG. 3A are combined, the combined magnetic field on the right side becomes stronger than the combined magnetic field on the left side. As a result, as shown in FIG. 3D, the field free area 2 moves to the left side. On the other hand, when the electrical current is adjusted such that a magnetic field flowing from the zero magnetic-field scan coil 14a towards the zero magnetic-field scan coil 14b and a magnetic field flowing from the zero magnetic-field scan coil 14c towards the zero magnetic-field scan coil 14d are generated, the field free area 2 moves to the right side.

At the same time, for example, it is assumed that the current flowing through each coil is adjusted such that a magnetic field flowing from the zero magnetic-field scan coil 14c towards the zero magnetic-field scan coil 14a and a magnetic field flowing from the zero magnetic-field scan coil 14d towards the zero magnetic-field scan coil 14b are generated. In this case, as shown in FIG. 3E, a magnetic field flowing from the feet end to the head end is generated. When the generated magnetic field and the magnetic field 6c shown in FIG. 3A are combined, the combined magnetic field on the feet end becomes stronger than the combined magnetic field on the head end. As a result, as shown in FIG. 3F, the field free area 2 moves to the feet end. On the other hand, when the electrical current is adjusted such that a magnetic field flowing from the zero magnetic-field scan coil 14a towards the zero magnetic-field scan coil 14c and a magnetic field flowing from the zero magnetic-field scan coil 14b towards the zero magnetic-field scan coil 14d are generated, the field free area 2 moves to the head end.

In this way, the field free area 2 can be moved in the horizontal direction and the head and feet direction by the electrical currents flowing through the zero magnetic-field scan coils 14a to 14d being respectively adjusted. Although explanations are omitted herein, the field free area 2 can be similarly moved when the zero magnetic-field scan coils 14e to 14h disposed on the lower surface of the inner wall of the frame 11 are used.

In the configuration of the zero magnetic-field scan coils 14a to 14h, described above, the field free area 2 cannot be moved vertically. However, the position of the field free area 2 can be equivalently moved within the subject P by the top plate 12 being moved in the vertical direction.

Figure 4A:
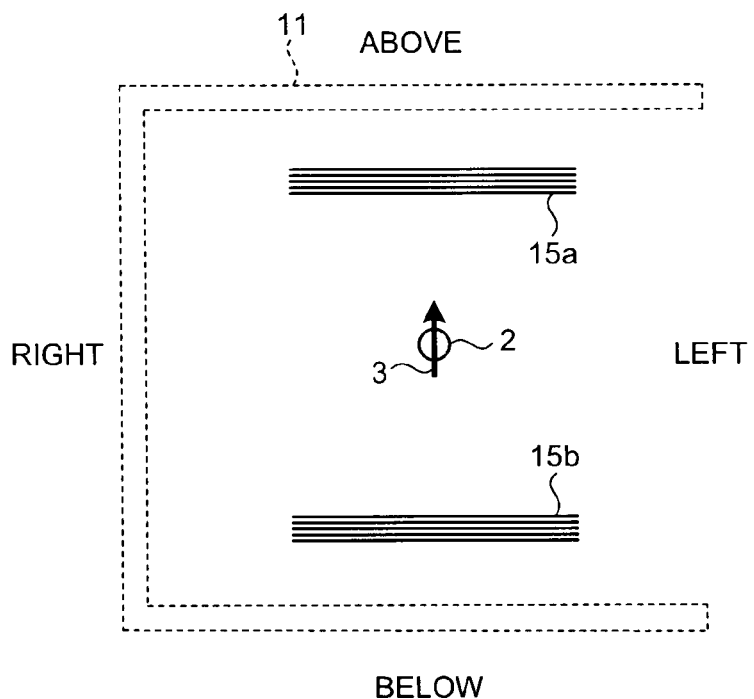
FIGS. 4A and 4B are diagrams explaining modulation coils.
Figure 4B:
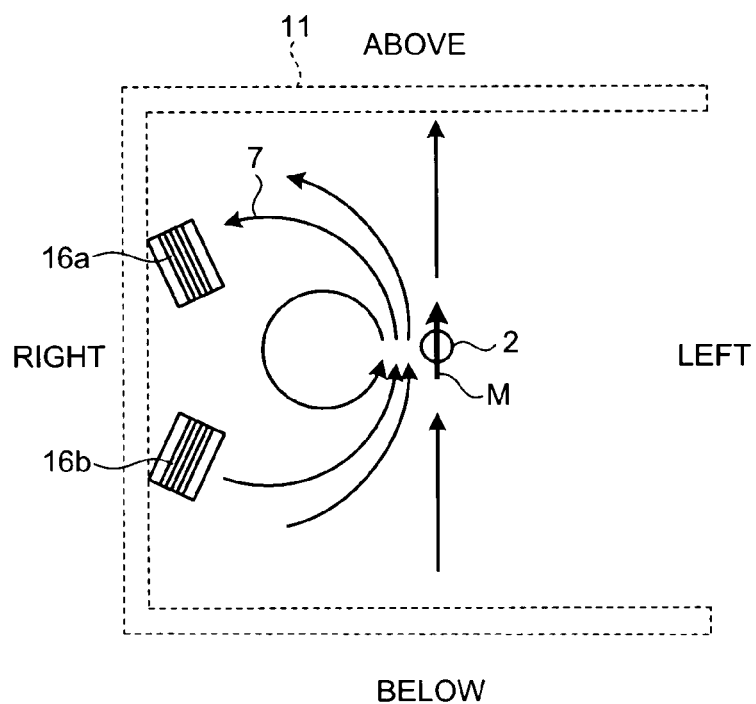

The modulation coils 15a and 15b are coils that magnetize magnetic particles by applying a modulation magnetic field. Specifically, the modulation coils 15a and 15b are electromagnets used to apply a modulation magnetic field in the area surrounded by the frame 11. The modulation coils 15a and 15b apply a modulation magnetic field of, for example, about 10 kilohertz to 100 kilohertz. FIGS. 4A and 4B are diagrams for explaining the modulation coils 15a and 15b. As shown in FIG. 4A, the modulation coils 15a and 15b are respectively disposed on an upper side and a lower side of the area surrounded by the frame 11. The modulation coils 15a and 15b are disposed facing each other. The modulation coils 15a and 15b apply the modulation magnetic field 3 from the lower side towards the upper side.

When the modulation coils 15a and 15b apply the modulation magnetic field 3, the magnetic particles present within the field free area 2 are magnetized and magnetization M occurs, as shown in FIG. 4B. A magnetic field 7 is thus generated from the field free area 2 with the magnetization of the magnetic particles. A waveform of the magnetic field 7 is the same as a waveform of the magnetization M. The waveform includes distortion depending on an amount of magnetic particles present within the field free area 2.

Figure 5A:
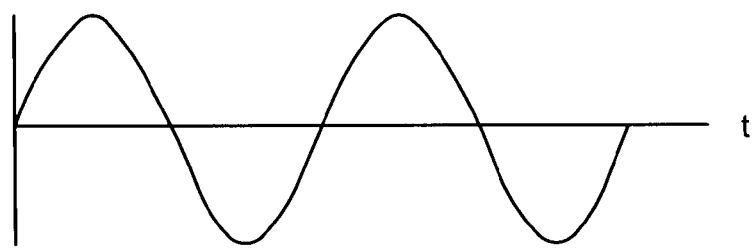
FIGS. 5A to 5C are schematic diagrams indicating waveforms of a magnetic field generated from a field free area.
Figure 5B:
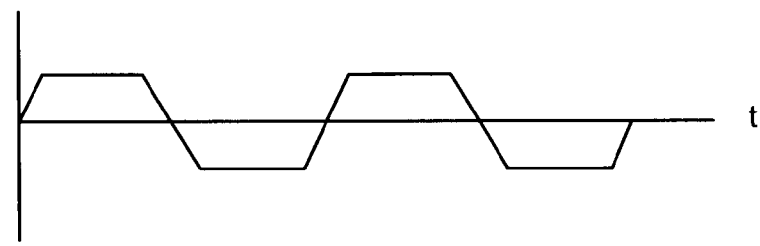
Figure 5C:
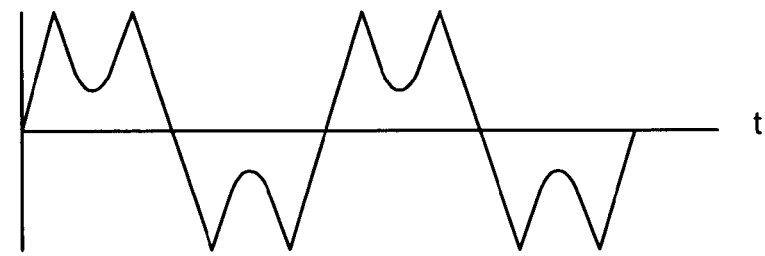

FIGS. 5A to 5C are schematic diagrams of a waveform of the magnetic field generated from the field free area 2. FIG. 5A is a schematic diagram of an intensity H of the magnetic field at the field free area 2. FIG. 5B is a schematic diagram of change in magnetic flux density B at the field free area 2. FIG. 5C is a schematic diagram of change in the magnetization M at the field free area 2.

The intensity H of the magnetic field generated near the field free area 2 is a sum of an intensity of the magnetic field generated by the permanent magnets 13a and 13b and the intensity of the modulation magnetic field generated by the modulation coils 15a and 15b. However, because the magnetic field generated by the permanent magnets 13a and 13b at the field free area 2 is zero, the waveform of the intensity H of the magnetic field is a sine wave, as shown in FIG. 5A. At the same time, the magnetic flux density B reaches a plateau at a predetermined saturated magnetic flux density as shown in FIG. 5B, as a result of magnetic saturation. Therefore, the magnetization M has a distorted waveform as shown in FIG. 5C because the magnetization M is a difference between B and $\mu_0$.

The detection coils 16a and 16b are electromagnets used to detect an interlinking magnetic flux. When the detection coils 16a and 16b are disposed in arbitrary positions within the area surrounded by the frame 11, the magnetic flux detected by the detection coils 16a and 16b includes, not only the magnetic flux of the magnetic field 7 generated by the magnetization M of the magnetic particles, but the magnetic flux of the magnetic fields 6a and 6b generated by the permanent magnets 13a and 13b and the magnetic flux of the modulation magnetic field 3 applied by the modulation coils 15a and 15b.

However, only the magnetic flux of the magnetic field 7 generated by the magnetization M of the magnetic particles is required to form an image of the distribution of the magnetic particles. The magnetic fields 6a and 6b generated by the permanent magnets 13a and 13b are both static magnetic fields. Therefore, frequencies of the magnetic fields 6a and 6b significantly differ from the magnetic field 7 generated by the magnetization M. As a result, the magnetic flux of the magnetic fields 6a and 6b and the magnetic flux of the magnetic field 7 can be easily separated by a known technology.

On the other hand, when taking into consideration clinical application, the modulation magnetic field 3 generated by the modulation coils 15a and 15b is, as described earlier, significantly larger than the magnetic field 7 generated by the magnetization M of the magnetic particles, as described above. Therefore, separation of these magnetic fields is difficult.

Therefore, in the magnetic particle imaging apparatus 10 according to the first embodiment, the detection coils 16a and 16b are disposed such that detection of the modulation magnetic field 3 applied by the modulation coils 15a and 15b is kept to a minimum (zero in terms of design) and the magnetic field 7 generated by the magnetization M of the magnetic particles can be efficiently detected. As a result, sufficient detection sensitivity can be achieved even in clinical application.

Figure 6:
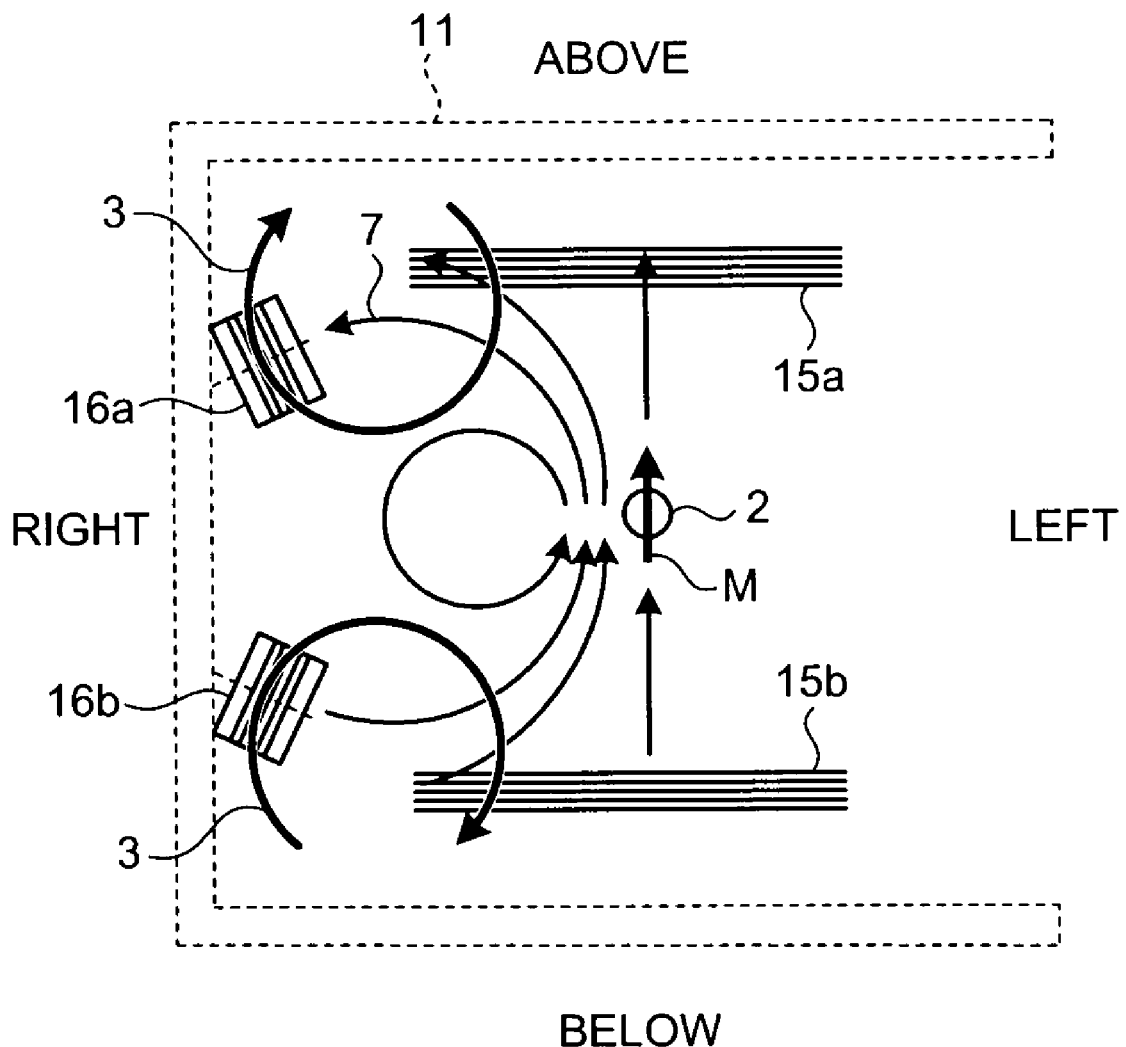
FIG. 6 is a diagram of an arrangement of detection coil according to the first embodiment.

An arrangement of the detection coils 16a and 16b will be described in detail hereafter. FIG. 6 is a diagram of an arrangement of the detection coils 16a and 16b according to the first embodiment. As shown in FIG. 6, in the magnetic particle imaging apparatus 10 according to the first embodiment, the detection coil 16a is disposed on an upper right side of the area surrounded by the frame 11. The detection coil 16b is disposed on the lower right side. Both detection coils 16a and 16b are disposed on outer sides of the modulation coils 15a and 15b.

Here, the detection coil 16a is disposed such that mutual inductance with the modulation coil 15a becomes substantially zero. The detection coil 16b is disposed such that mutual inductance with the modulation coil 15b becomes substantially zero.

Specifically, according to the first embodiment, the detection coil 16a is disposed such that an axis (center axis) running through a center of a coil surface of the detection coil 16a is approximately orthogonal to the magnetic flux of the modulation magnetic field 3 applied by the modulation coil 15a to make mutual inductance between the detection coil 16a and the modulation coil 15a substantially zero. The detection coil 16b is disposed such that an axis (center axis) running through a center of a coil surface of the detection coil 16b is approximately orthogonal to the magnetic flux of the modulation magnetic field 3 applied by the modulation coil 15b to make mutual inductance between the detection coil 16b and the modulation coil 15b substantially zero.

Because the detection coils 16a and 16b are disposed as described above, the magnetic flux of the modulation magnetic field 3 applied by the modulation coils 15a and 15b is not interlinked with the detection coils 16a and 16b. As a result, an influence on the detection coils 16a and 16b by the magnetic flux of the modulation magnetic field 3 applied by the modulation coils 15a and 15b is restrained.

At the same time, the center axis of each detection coil 16a and 16b is not approximately orthogonal to the magnetic flux of the magnetic field 7 generated by the magnetization M of the magnetic particles (which means that the coil surface of each detection coil 16a and 16b approximately orthogonal to the magnetic flux of the magnetic field 7). Therefore, the detection coils 16a and 16b have a very low detection sensitivity to the modulation magnetic field 3 applied by the modulation coils 15a and 15b, and have a certain amount of detection sensitivity to the magnetic field 7 generated by the magnetization M of the magnetic particles.

Figure 7:
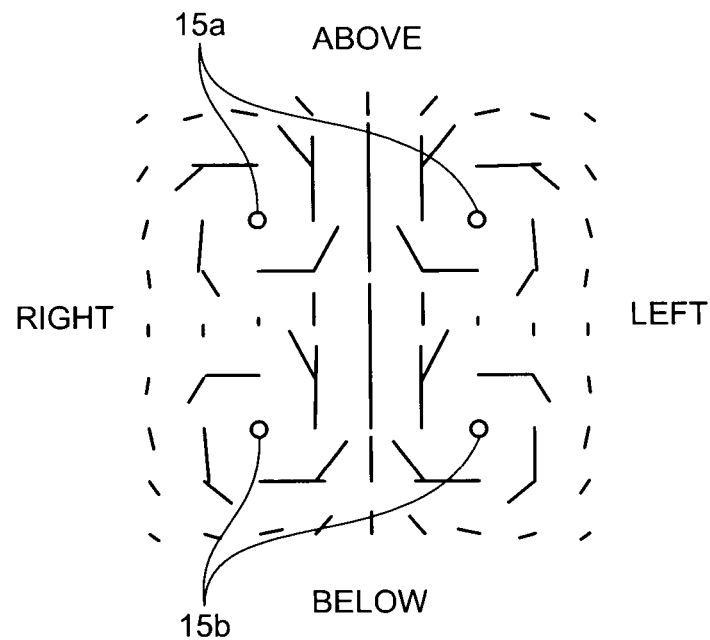
FIG. 7 is a distribution diagram of distribution of a modulation magnetic field applied by modulation coils.

A method of disposing the detection coils 16a and 16b will be described hereafter. Specifically, first, a predetermined number of points are defined within the area surrounded by the frame 11. The points are referred to as "measurement points". Next, the intensity and direction of the modulation magnetic field 3 applied by the modulation coils 15a and 15b are calculated at each measurement point. FIG. 7 is a distribution diagram of a distribution of the modulation magnetic field 3 applied by the modulation coils 15a and 15b. A direction of each straight line shown in FIG. 7 indicates the direction of the modulation magnetic field 3 at each measurement point. A length of each straight line indicates an intensity of the modulation magnetic field 3 at each measurement point.

Then, any one of measurement points is selected from among the defined measurement points. The detection coil is disposed so that the center point of the detection coil overlaps with the selected measurement point and the center axis of the detection coil is approximately orthogonal to the direction of the modulation magnetic field 3 at the selected measurement point.

Figure 8:
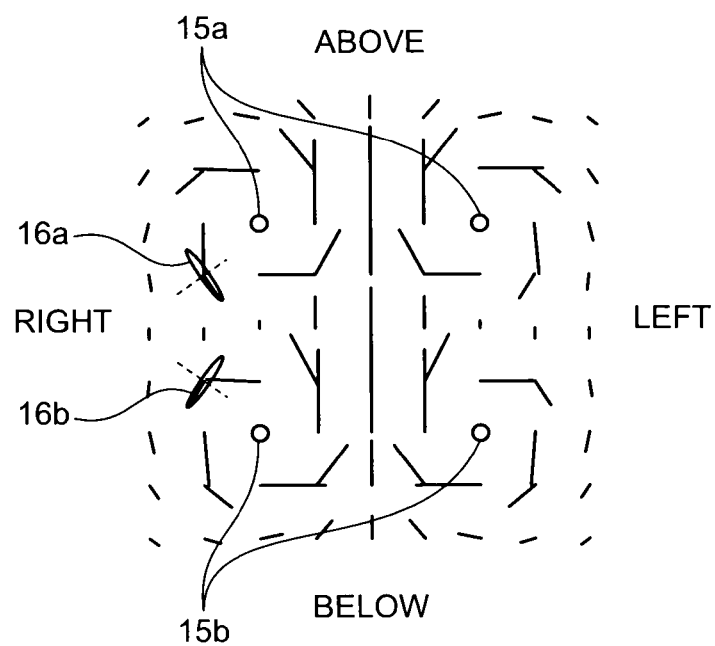
FIG. 8 is a diagram of an arrangement example of the detection coil shown in FIG. 6.

FIG. 8 is a diagram of an arrangement example of the detection coils 16a and 16b shown in FIG. 6. For example, as shown in FIG. 8, a measurement point is selected from the upper side and from the lower side, among the measurement points on the right side of the area surrounded by the frame 11 and the outer sides of the modulation coils 15a and 15b. The detection coils 16a and 16b are disposed based on each measurement point.

The detection coils 16a and 16b are disposed in this way such that the center axis of the detection coil is approximately orthogonal to the magnetic flux of the modulation magnetic field 3 applied by the modulation coils 15a and 15b. As a result, the magnetic flux detected by the detection coils 16a and 16b, among the magnetic flux of the modulation magnetic field 3 generated by the modulation coils 15a and 15b, can be suppressed to a minimum.

In above example, detection coil is located approximately orthogonal to the magnetic flux of the modulation magnetic field 3. To explain it more generally, the arrangement of detection coils are made so that the mutual inductance of detection coils and modulation coils are suppressed to a minimum.

Returning to FIG. 1, the image processing unit 30 generates an image indicating the distribution of the magnetic particles based on the change in the magnetic flux detected by the detection coils 16a and 16b. The image processing unit 30 outputs the generated image to, for example, a display device such as a monitor and an output device such as a printer.

As described above, according to the first embodiment, the detection coils 16a and 16b that detect the change in the interlinking magnetic flux are disposed such as to suppress the influence of the magnetic flux of the modulation magnetic field 3 applied by the modulation coils 15a and 15b and included in the detected magnetic flux. Therefore, the detection sensitivity of the detection coil can be enhanced. Sufficient sensitivity can be achieved for clinical application.

According to the first embodiment, when the detection coils 16a and 16b are disposed such that the center axes are approximately orthogonal to the direction of the modulation magnetic field 3 generated by the modulation coils 15a and 15b is described. However, the present invention is not limited thereto. Various other detection coil disposal methods can be considered. Hereafter, other examples of the detection coil disposal will be described with reference to FIG. 9 to FIG. 12.

Figure 9:
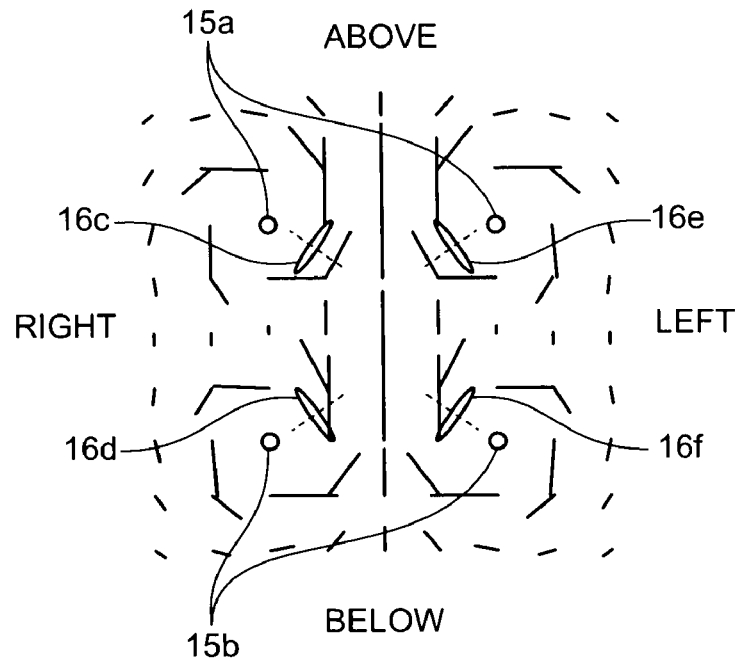
FIG. 9 is a diagram (1) of another arrangement example of the detection coil.

FIG. 9 is a diagram (1) of another arrangement example of the detection coil. For example, the detection coils can be disposed on inner sides of the modulation coils 15a and 15b. In the example, four detection coils 16c to 16f are each disposed based on measurement points on the inner sides of the modulation coils 15a and 15b.

Signal detection sensitivity can be further enhanced when the detection coils 16c to 16f are disposed on the inner sides of the modulation coils 15a and 15b, because each detection coil is disposed closer to the magnetization M than when the detection coils 16c to 16f are disposed on the outer sides.

With reference to the distribution diagram in FIG. 7, it is understood that a measurement point is present at which the magnetic field becomes zero as a result of the modulation magnetic field 3 applied by the modulation coil 15a and the modulation magnetic field 3 applied by the modulation coil 15b being mutually cancelled. As a result of the detection coils 16c to 16f being disposed as described above, the modulation magnetic field 3 applied by the modulation coils 15a and 15b and interlinked with the detection coils 16c to 16f can become zero.

Figure 10:
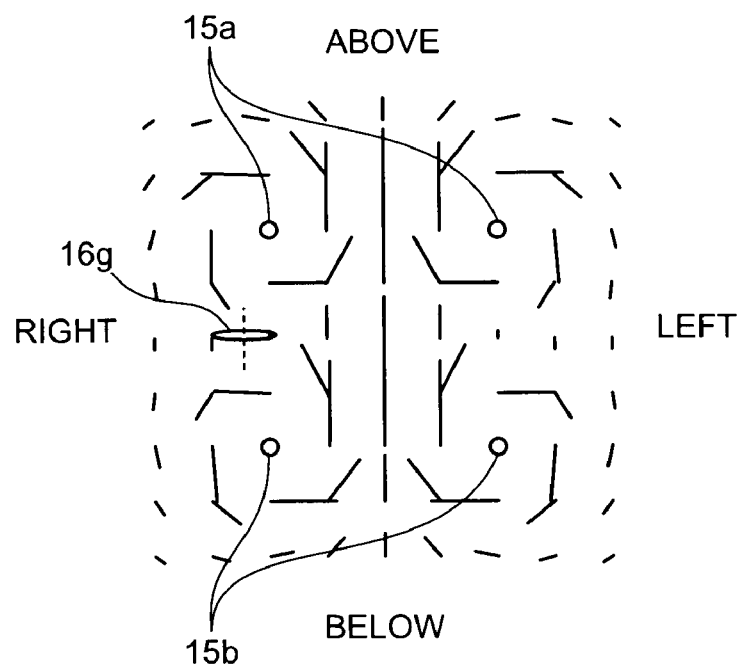
FIG. 10 is a diagram (2) of another arrangement example of the detection coil.

FIG. 10 is a diagram (2) of another arrangement example of the detection coil. For example, as shown in FIG. 10, a detection coil 16g is disposed in a position at which the modulation magnetic field 3 generated on the right side of the modulation coil 15a and the modulation magnetic field 3 generated on the right side of the modulation coil 15b are mutually cancelled. In this case, regardless of the direction in which the detection coil 16g is disposed, the modulation magnetic field 3 interlinked with the detection coil 16g become zero. However, to efficiently detect the magnetic flux of the magnetic field 7 generated by the magnetization M of the magnetic particles, the detection coil 16g is preferably disposed in a direction in which a coil surface is perpendicular to the magnetic flux of the magnetic field 7. The magnetic flux of the magnetic field 7 interlinked with the detection coil reaches maximum when the detection coil 16g is disposed in this way. Therefore, the detection sensitivity to the magnetic field 7 of the detection coil also reaches maximum.

Alternatively, the modulation magnetic field 3 applied by the modulation coils 15a and 15b can be made zero through use of two serially connected detection coils wound in opposite directions.

Figure 11:
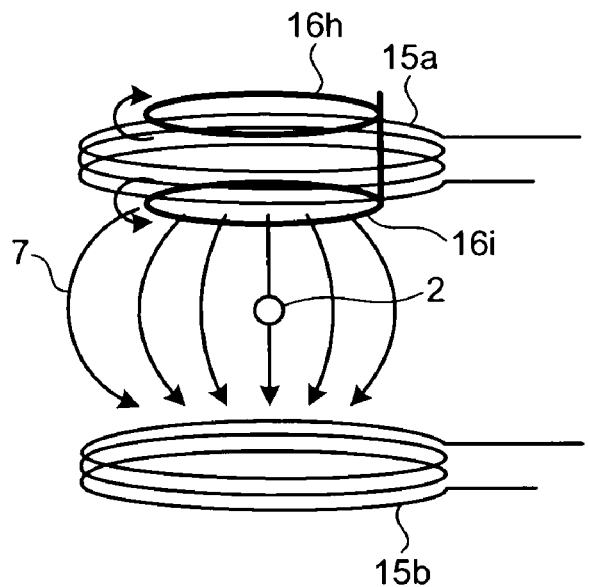
FIG. 11 is a diagram (3) of another arrangement example of the detection coil.

FIG. 11 is a diagram (3) of another arrangement example of the detection coil. For example, as shown in FIG. 11, serially connected detection coils 16h and 16i wound in opposite directions are respectively disposed above and below the modulation coil 15a. Here, each detection coil has a same coil surface area and a same number of windings. Each detection coil is disposed at a same distance from the modulation coil 15a such that the center axis of each detection coil matches the center axis of the modulation coil 15a.

As a result of the detection coils 16h and 16i being disposed in this way, the modulation magnetic fields 3 applied by the modulation coils 15a and 15b and detected by each detection coil are mutually cancelled. Therefore, when the detection coils 16h and 16i are considered to be a single detection coil, the modulation magnetic field 3 interlinked with the entire detection coil can be considered to be zero.

On the other hand, regarding the magnetic field 7 generated by the magnetization M, because the detection coil 16i is disposed closer to the field free area 2 than the detection coil 16h, the magnitude of the interlinking magnet field differs for each detection coil. As a result, even when the detection coils 16h and 16i are considered to be a single detection coil, the magnetic field 7 interlinked with the entire detection coil is not zero. Therefore, a difference occurs in the magnetic field 7 interlinked with each detection coil. By detecting the difference, the magnetic field 7 generated by the magnetization M can be detected.

Here, the detection coils 16h and 16i have the same coil surface area and the same number of windings. Each detection coil is disposed at a same distance from the modulation coil 15a such that the center axis of each detection coil matches the center axis of the modulation coil 15a. However, the coil surface area, the number of windings, and the disposal positions are not limited thereto.

In other words, even when each detection coil is disposed in a position that is a different distance from the modulation coil 15a, the modulation magnetic field 3 interlinking the entire detection coil can be made zero by the coil surface areas and the number of windings being changed such that the modulation magnetic fields 3 interlinked with each detection coil are mutually cancelled. At this time, each detection coil is preferably disposed such that a total of the magnetic field 7 generated by the magnetization M is as large as possible.

Alternatively, compensation coils can be serially inserted into each modulation coil and detection coil and disposed such as to face each other. As a result, the modulation magnetic field 3 applied by the modulation coils 15a and 15b can become zero.

Figure 12:
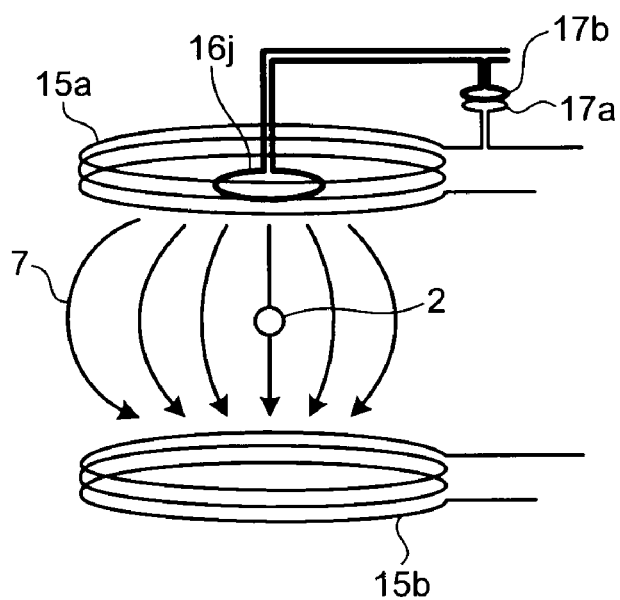
FIG. 12 is a diagram (4) of another arrangement example of the detection coil.

FIG. 12 is a diagram (4) of another arrangement example of the detection coil. For example, as shown in FIG. 12, compensation coils 17a and 17b are inserted in a series with the modulation coil 15a. The compensation coil 17a is inserted in a series with a detection coil 16j. At this time, the compensation coils 17a and 17b are disposed such as to face each other. A ratio of the number of windings between the compensation coils 17a and 17b are set such that a sum of a magnetic flux interlinked with the detection coil 16j among the magnetic flux of the modulation magnetic field 3 applied by the modulation coils 15a and 15b and a magnetic flux interlinked with the compensation coil 17b and generated by the compensation coil 17a becomes zero.

The method using the compensation coils as in the example in FIG. 12 is useful for making fine adjustments to make a total amount of the magnetic flux of the modulation magnetic field 3 applied by the modulation coils 15a and 15b, among the magnetic flux detected by the detection coil, zero. The method is effective when used in combination with each of the above-described examples.

According to the first embodiment, when the interlinking magnetic flux, among the magnetic flux of the modulation magnetic field 3 applied by the modulation coils 15a and 15b, is minimized through adjustment of the position and the direction when the detection coil is disposed is described. However, even when a design is achieved such as to dispose the detection coil as described above, mechanical error may occur during manufacture. Therefore, it is difficult for the magnetic field interlinking with the detection coil and generated by the modulation coils 15a and 15b to be made completely zero.

Therefore, according to a second embodiment, following configuration and method are described. In the configuration and method, a feedback coil is provided for adjusting a balance in the modulation magnetic field applied by the modulation coils 15a and 15b. The feedback coil is driven based on a result actually detected by the detection coil. As a result, the magnetic field interlinked with the detection coil and generated by the modulation coils 15a and 15b is made completely zero. Here, for convenience of explanation, functional sections achieving same purposes as each section in FIG. 1 are given the same reference numbers. Detailed explanations thereof are omitted.

Figure 13:
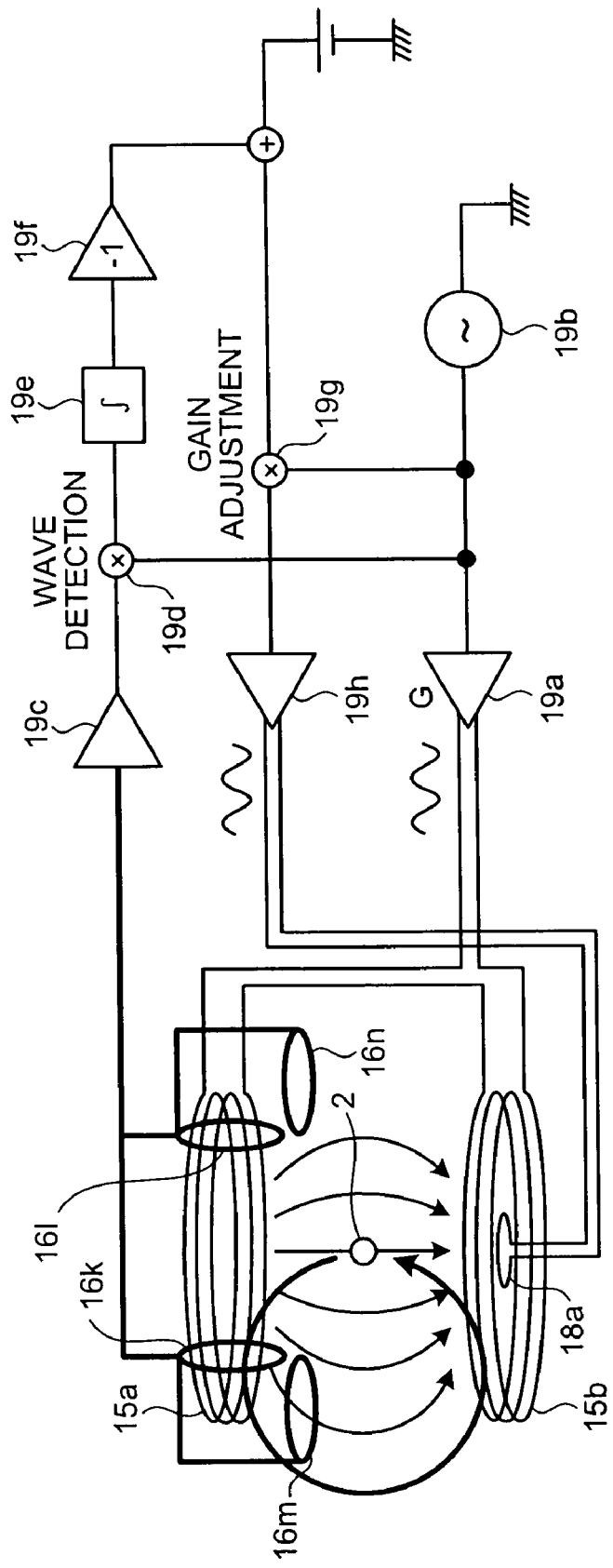
FIG. 13 is a diagram for explaining control of a feedback coil according to a second embodiment.

FIG. 13 is a diagram for explaining control of the feedback coil according to the second embodiment. Four serially connected detection coils 16k to 16n are disposed, in which two detection coils 16k and 16l on the inner side of the modulation coil 15a and two detection coils 16m and 16n on the outer side of the modulation coil 15b. A feedback coil 18a is disposed in an approximate center of the modulation coil 15b.

Here, the modulation coils 15a and 15b are driven by a modulation signal supplied by an alternating current power supply 19b, via an amplifier circuit 19a. The modulation signal is generally almost a sine wave. However, the modulation signal actually includes some harmonic components for ON/OFF control of the signal, pulse drive, and the like.

A signal detected by the detection coils 16k to 16n is inputted into a detection circuit 19d, via the amplifier circuit 19c. The detection circuit 19d performs wave detection on the inputted signal using a signal waveform of the electrical current flowing through the modulation coils 15a and 15b. As a result, a basic frequency element is extracted from the inputted signal. A signal of the basic frequency element extracted by the detection circuit 19d is inputted into an integration circuit 19e.

The integration circuit 19e integrates inputted signals and inputs an integration result into a gain adjusting circuit 19g, via an amplifier circuit 19f. The gain adjusting circuit 19g generates a modulation signal of a same frequency waveform as the modulation signal driving the modulation coils 15a and 15b, using the integration result as gain. Based on the generated modulation signal, the modulation signal is supplied to the feedback coil 18a, via an amplifier circuit 19h.

The above described circuit configuration configures a primary delay system. The primary delay system performs control such that an element with a same frequency as those of the modulation coils 15a and 15b, among the magnetic flux interlinked with the detection coils 16k to 16n, becomes zero. In the configuration, even when a mechanical error occurs, the magnetic field generated by the feedback coil 18a is controlled such as to cancel the mechanical error. Therefore, a measurement signal from the detection coil of the modulation magnetic field generated by the modulation coils can be made zero. At the same time, the harmonic component included in the magnetic field generated by the magnetization M remains without being cancelled. Therefore, signal detection accuracy does not deteriorate.

As described above, according to the second embodiment, the modulation coils 15a and 15b are driven using the modulation signal waveform. The element synchronous with the modulation signal waveform is extracted from the signal detected by the detection coil. The feedback coil 18a is controlled such that the synchronous element becomes zero. Therefore, the signal detected by the detection coil within the modulation magnetic field generated by the modulation coils 15a and 15b can be significantly reduced, and the detection sensitivity of the detection coil can be further enhanced.

Figure 14:
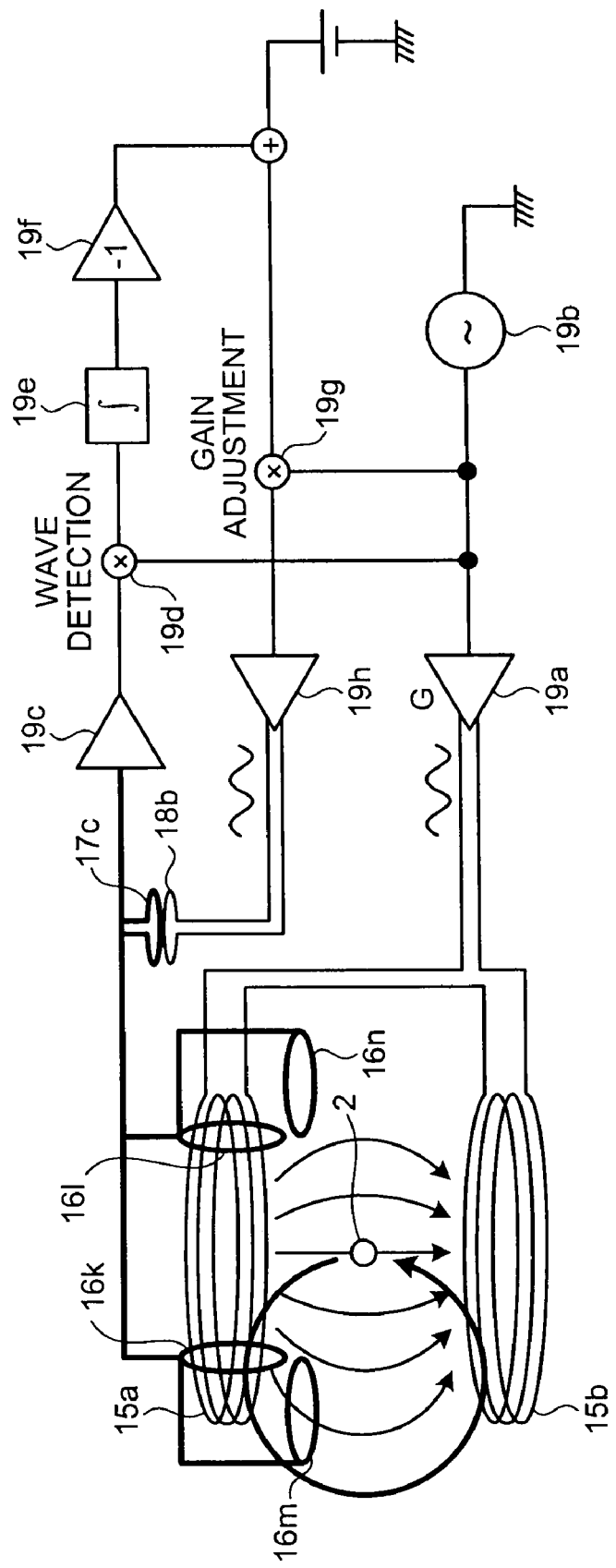
FIG. 14 is a diagram of another arrangement example of a feedback coil.

According to the second embodiment, when the feedback coil 18a is provided in the approximate center of the modulation coil 15b is described. However, the present invention is not limited thereto. For example, a compensation coil can be connected to the detection coil. The feedback coil can be disposed such as to face the compensation coil. FIG. 14 is another arrangement example of feedback coil.

Specifically, for example as shown in FIG. 14, a compensation coil 17c is inserted between the detection coils 16k to 16n and an amplifier circuit 19c. A feedback coil 18b is disposed such as to face the compensation coil 17c. A modulation signal generated by the gain adjusting circuit 19g and having a same waveform as the modulation signal driving the modulation coils 15a and 15b is supplied to the feedback coil 18b.

As a result, a magnetic flux canceling the error is generated from the feedback coil 18b. Control is performed such that the element with the same frequency as those of the modulation coils 15a and 15b, among the magnetic flux interlinked with the detection coils 16k to 16n, becomes zero.

Alternatively, the modulation signal generated by the gain adjusting circuit 19g can be directly applied to one of either the modulation coil 15a or the modulation coil 15b. The magnetic flux canceling the error is generated from the modulation coil to which the modulation signal is applied. Control is performed such that the element with the same frequency as those of the modulation coils 15a and 15b, among the magnetic flux interlinked with the detection coils 16k to 16n, becomes zero.

The present invention according to the first embodiment and the second embodiment has been described above. According to these embodiments, the modulation coils 15a and 15b are described in which the detection coils are disposed near the permanent magnets 13a and 13b. However, the present invention can be similarly applied when the modulation coils have a different configuration.

Figure 15:
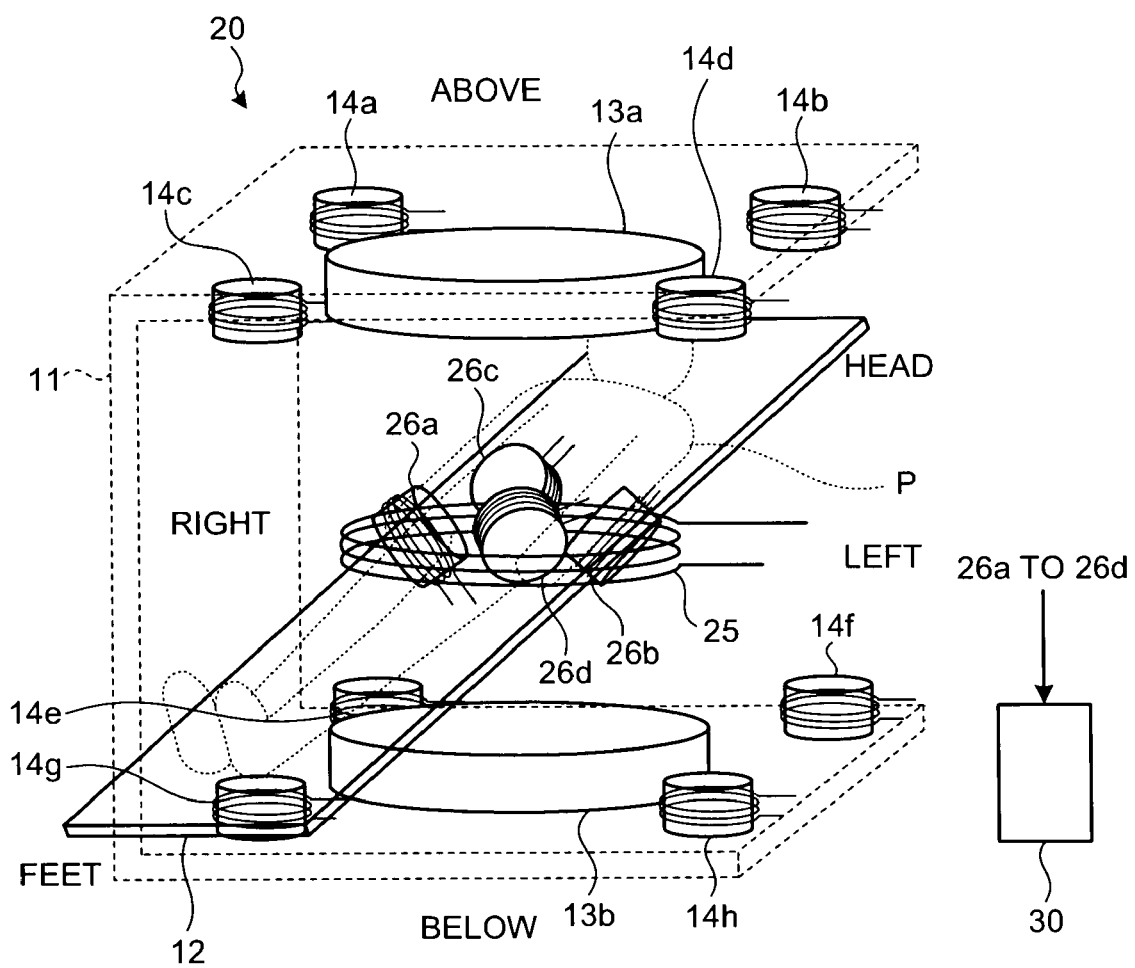
FIG. 15 is a diagram of another example of the configuration of the magnetic particle imaging apparatus.
Figure 16:
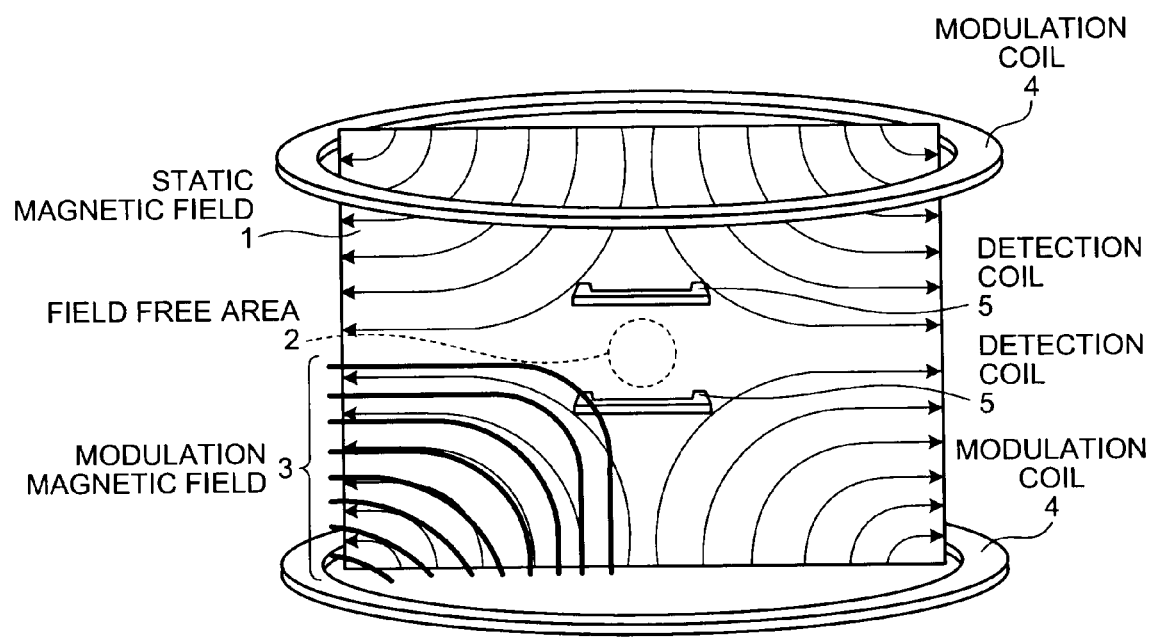
FIG. 16 is a diagram for explaining a principle of the magnetic particle imaging apparatus.

FIG. 15 is another example of the configuration of the magnetic particle imaging apparatus. In a magnetic particle imaging apparatus 20, a modulation coil 25 and detection coils 26a to 26d are each disposed on the top plate 12. A three-dimensional scan is performed during image scanning by the top plate 12 being gradually moved upwards and downwards. Moreover, the top plate 12 can be moved in a head direction and a feet direction.

The modulation coil 25 and the detection coils 26a to 26d move with the movement of the top plate 12. Therefore, each coil is constantly disposed close to the subject P, thereby further enhancing the detection sensitivity.

In this case, same as the first embodiment, various patterns can be considered regarding positions and directions when the detection coils are disposed. For example, in the example in FIG. 15, the detection coils 26a to 26d are disposed in the same positions as the detection coils 16d to 16f in FIG. 9.

As can be analogized by the examples above, the present invention can be similarly applied with various modulation coil and detection coil configurations.

As described above, in the magnetic particle imaging apparatus according to the present invention, the detection coil does not detect the magnetic flux generated by the modulation coil. The detection coil can efficiently extract and detect the magnetic field generated from an area to be imaged. Therefore, the detection sensitivity is significantly enhanced. In a conventional configuration, actualization of an imaging device for humans has been considered difficult. However, through use of the present invention, sensitivity can be significantly enhanced. An imaging apparatus that can be applied to clinical situations can be actualized.

In the conventional configuration of the imaging apparatus, highly concentrated magnetic particles are used. A lesion can be detected only when the lesion becomes very large. However, through use of the present invention, detection can be performed even when concentration of the magnetic particles on an affected area is less than that in the conventional configuration. In addition, magnetic particles concentrated in a small area (affected area) can be detected. Therefore, milder diseases and diseases at an earlier stage can be detected, thereby contributing to improvement in diagnostic quality.

The present invention has been achieved to solve the above described problems and issues of the above described conventional technologies. An object of the invention is to provide a magnetic particle imaging apparatus, a signal detecting method, and a signal detecting apparatus for the magnetic particle imaging apparatus that can be applied to a clinical situation through enhancement of detection sensitivity of a detection coil.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A magnetic particle imaging (MPI) apparatus configured for imaging a subject, comprising:
    a magnet unit that generates a magnetic field in order to form a non-magnetic field area within a detection space;
    a modulation coil that magnetizes magnetic particles that have been injected into the subject by applying a modulation magnetic field into the detection space into which the subject can be placed;
    a detection coil within the detection space that detects a change in a magnetic flux in the injected magnetic particles, the detection coil being interlinked with the modulation coil and is disposed in order to suppress an influence caused by a magnetic flux of the modulation magnetic field applied by the modulation coil and included in the detected magnetic flux; and an image processing unit that forms an image of a distribution of the magnetic particles based on the change in the magnetic flux in the injected magnetic particles detected by the detection coil, wherein the detection coil is disposed positionally fixed in order to align a center axis of the detection coil running through a center of the detection coil to be substantially orthogonal to magnetic flux of the modulation magnetic field being applied by the modulation coil at an intersection defined by where the magnetic flux and the center axis of the detection coil cross one another, in the detection space, so that mutual inductance produced with the modulation coil becomes substantially zero.

2. The apparatus according to claim 1 further comprising a feedback coil that applies a magnetic field that adjusts a magnitude of the magnetic flux of the modulation magnetic field applied by the modulation coil, based on the magnetic flux of the modulation magnetic field included in the magnetic flux detected by the detection coil.

3. The apparatus according to claim 2, wherein the detection coil has a compensation coil serially connected to the detection coil; and the feedback coil adjusts the magnitude of the magnetic flux of the modulation magnetic field by applying a magnetic field to the compensation coil of the detection coil.

4. The apparatus according to claim 1, wherein the detection coil is disposed such that a center axis of the detection coil is approximately orthogonal to the magnetic flux of the modulation magnetic field applied by the modulation coil.

5. The apparatus according claim 4 further comprising a feedback coil that applies a magnetic field that adjusts a magnitude of the magnetic flux of the modulation magnetic field applied by the modulation coil, based on the magnetic flux of the modulation magnetic field included in the magnetic flux detected by the detection coil.

6. The apparatus according to claim 5, wherein the detection coil has a compensation coil serially connected to the detection coil; and the feedback coil adjusts the magnitude of the magnetic flux of the modulation magnetic field by applying a magnetic field to the compensation coil of the detection coil.

7. The apparatus according to claim 1, wherein the detection coil is disposed on an outer side of the modulation coil.

8. The apparatus according to claim 1, wherein the detection coil is disposed on an inner side of the modulation coil.

9. The apparatus according to claim 1, wherein the modulation coil includes at least two coils; and
the detection coil is disposed in a position at which modulation magnetic fields applied by each coil forming the modulation coil are mutually cancelled.

10. The apparatus according to claim 9, wherein the detection coil is disposed such that a coil surface of the detection coil is approximately orthogonal to the magnetic flux generated by magnetization of magnetic particles present in the non-magnetic field area.

11. The apparatus according to claim 1, wherein the detection coil includes at least two serially connected coils, in which each coil is disposed such that the magnetic flux of the modulation magnetic fields included in the detected magnetic flux are mutually cancelled.

12. The apparatus according to claim 1, wherein the detection coil includes a first compensation coil serially connected to the detection coil; and
the modulation coil includes a second compensation coil that is serially connected to the modulation coil and applies a magnetic field to the first compensation coil such that the magnetic flux of the modulation magnetic fields included in the magnetic flux detected by the detection coil are mutually cancelled.

13. A method of disposing a detection coil for a magnetic particle imaging (MPI) apparatus for imaging a subject, the method comprising:
disposing a modulation coil that magnetizes magnetic particles that have been injected into the subject by generating a modulation magnetic field into a detection space into which the subject can be placed and disposing a detection coil with the detection space that detects a change in a magnetic flux in the injected magnetic particles, the detection coil being interlinked with the modulation coil, such that an influence caused by a magnetic flux of the modulation magnetic field applied by the modulation coil and included in the detected magnetic flux is suppressed, wherein the detection coil is positionally fixed in order to align a center axis of the detection coil running through a center of the detection coil to be substantially orthogonal to magnetic flux of the modulation magnetic field being applied by the modulation coil, in the detection space, so that mutual inductance produced with the modulation coil becomes substantially zero.

14. The method according to claim 13, wherein the detection coil is disposed such that a center axis of the detection coil is approximately orthogonal to the magnetic flux of the modulation magnetic field applied by the modulation coil.

15. The method according to claim 13, wherein the modulation coil includes at least two coils; and
the detection coil is disposed in a position at which modulation magnetic fields applied by each coil forming the modulation coil are mutually cancelled.

16. The method according to claim 15, wherein the detection coil is disposed such that a coil surface of the detection coil is approximately orthogonal to the magnetic flux generated by magnetization of magnetic particles present in the non-magnetic field area.

17. A magnetic flux detecting apparatus comprising: a modulation coil that magnetizes magnetic particles that have been injected into a subject by applying a modulation magnetic field into a detection space into which the subject can be placed; and
a detection coil that detects a change in a magnetic flux in the injected magnetic particles, the detection coil being interlinked with the modulation coil, and that is disposed in order to suppress an influence caused by a magnetic flux of the modulation magnetic field applied by the modulation coil and included in the detected magnetic flux, wherein the detection coil is positionally fixed in order to align a center axis of the detection coil running through a center of the detection coil to be substantially orthogonal to magnetic flux of the modulation magnetic field being applied by the modulation coil, in the detection space, so that mutual inductance produced with the modulation coil becomes substantially zero.

18. The apparatus according to claim 17, wherein the detection coil is disposed such that a center axis of the detection coil is approximately orthogonal to the magnetic flux of the modulation magnetic field applied by the modulation coil.

19. The apparatus according to claim 17, wherein the modulation coil includes at least two coils; and the detection coil is disposed in a position at which modulation magnetic fields applied by each coil forming the modulation coil are mutually cancelled.

20. The apparatus according to claim 19, wherein the detection coil is disposed such that a coil surface of the detection coil is approximately orthogonal to the magnetic flux generated by magnetization of magnetic particles present in the non-magnetic field area.

21. A magnetic particle imaging apparatus (MPI) configured for imaging a subject comprising:
- a magnet unit that generates a magnetic field in order to form a non-magnetic field area within a detection space;
- a modulation coil that magnetizes magnetic particles that have been injected into the subject by applying a modulation magnetic field into the detection space into which the subject can be placed;
- a detection coil within the detection space that detects a change in a magnetic flux in the injected magnetic particles, the detection coil being interlinked with the modulation coil and is disposed in order to suppress an influence caused by a magnetic flux of the modulation magnetic field applied by the modulation coil and included in the detected magnetic flux; and
- an image processing unit that forms an image of a distribution of the magnetic particles based on the change in the magnetic flux in the injected magnetic particles detected by the detection coil;

wherein the detection coil includes a first coil and a second coil that is serially connected to the first coil, the second coil cancelling the magnetic flux of the modulation magnetic field included in the magnetic flux detected by the first coil and thereby making mutual inductance substantially zero between the detection coil and the modulation magnetic field.

22. The apparatus according to claim 21, wherein the first and second coils of the detection coil are disposed in order to interpose the modulation coil between the first and the second coils of the detection coil, the first and the second coils of the detection coil each including a coil surface area and a number of windings and thereby making a modulation magnetic field detected by the detection coil substantially zero.

23. The apparatus according to claim 21, wherein the modulation coil includes a compensation coil serially connected to the modulation coil, the compensation coil disposed in order to face the second coil and thereby making a modulation magnetic field detected by the detection coil substantially zero.

* * * * *